(12) United States Patent
Ciomei et al.

(10) Patent No.: US 8,946,226 B2
(45) Date of Patent: *Feb. 3, 2015

(54) USE OF CDK INHIBITOR FOR THE TREATMENT OF GLIOMA

(75) Inventors: Marina Ciomei, Corsico (IT); Francesco Fiorentini, Milan (IT); Enrico Pesenti, Parabiago (IT)

(73) Assignee: Nerviano Medical Sciences S.r.l., Nerviano (MI) (IT)

( * ) Notice: Subject to any disclaimer, the term of this patent is extended or adjusted under 35 U.S.C. 154(b) by 895 days.

This patent is subject to a terminal disclaimer.

(21) Appl. No.: 13/055,533

(22) PCT Filed: Jul. 28, 2009

(86) PCT No.: PCT/EP2009/059747
§ 371 (c)(1),
(2), (4) Date: Mar. 18, 2011

(87) PCT Pub. No.: WO2010/012733
PCT Pub. Date: Feb. 4, 2010

(65) Prior Publication Data
US 2011/0190311 A1 Aug. 4, 2011

(30) Foreign Application Priority Data
Jul. 29, 2008 (EP) .................... 08161323

(51) Int. Cl.
*A61K 45/06* (2006.01)
*A61K 31/4188* (2006.01)
*A61K 31/519* (2006.01)

(52) U.S. Cl.
CPC ........... *A61K 31/519* (2013.01); *A61K 31/4188* (2013.01); *A61K 45/06* (2013.01)
USPC .................................................. 514/252.16

(58) Field of Classification Search
USPC ................. 514/49, 252.16; 544/371; 206/438
See application file for complete search history.

(56) References Cited

U.S. PATENT DOCUMENTS

| 8,518,930 B2 * | 8/2013 | Ciomei et al. ................ 514/185 |
| 2011/0224222 A1 * | 9/2011 | Ciomei et al. ........... 514/252.17 |

FOREIGN PATENT DOCUMENTS

| WO | WO 2004/104007 | * | 2/2004 | .......... C07D 487/04 |
| WO | WO 2004/104007 A1 | | 12/2004 | |
| WO | WO 2007/090794 | * | 2/2007 | .......... A61K 31/337 |
| WO | WO 2007/090794 A1 | | 8/2007 | |

OTHER PUBLICATIONS

Nieder C. et al., "Therapeutic Options for Recurrent High-Grade Glioma in Adult Patients: Recent Advances", *Critical Reviews in Oncology/Hematology* 60(3):181-193 (2006).
Liu R. et al., "Recent Advances in the Treatment of Central Nervous System Tumors", *Update on Cancer Therapeutics* 3(1):49-79 (2008).
Stupp R. et al., "Anaplastic Astrocytoma in Adults", *Critical Reviews in Oncology/Hematology* 63(1):72-80 (2007).
Senderowicz A.M., "Small-Molecule Cyclin-Dependent Kinase Modulators", *Oncogene* 22(42):6609-6620 (2003).
Newcomb E.W. et al., "Flavopiridol Inhibits the Growth of GL261 Gliomas In Vivo", *Cell Cycle* 3(2):230-234 (2004).
Komata T. et al., "Antitumour Effect of Cyclin-Dependent Kinase Inhibitors ($p16^{INK4A}$, $p18^{INK4C}$, $p19^{INK4D}$, $p21^{WAF1/CIP1}$ and $p27^{KIP1}$) on Malignant Glioma Cells", *British Journal of Cancer* 88(8):1277-1280 (2003).
International Search Report dated Sep. 28, 2009 from the European Patent Office.
Akiyama, "Molecular mechanism of cell cycle control", Nippon Rinsho, Apr. 1996, pp. 1031-1036, vol. 54, No. 4.

* cited by examiner

*Primary Examiner* — Erich A Leeser
(74) *Attorney, Agent, or Firm* — Scully, Scott, Murphy & Presser, P.C.

(57) ABSTRACT

The invention provides a low molecular weight ATP-competitive CDK inhibitor able to cross the blood brain barrier for use in the treatment of malignant glioma and, in particular, of glioblastoma. The compound can be administered together with one or more agents selected from the group consisting of cytotoxic or cytostatic agents and ionizing radiation.

2 Claims, 3 Drawing Sheets

USE OF CDK INHIBITOR FOR THE TREATMENT OF GLIOMA

TECHNICAL FIELD

The present invention relates to the treatment of glioma patients through the use of a low molecular weight ATP-competitive CDK (Cyclin-Dependent Kinase) inhibitor able to cross the blood brain barrier.

BACKGROUND ART

Malignant gliomas are highly invasive and neurologically destructive tumors, whose most aggressive manifestation is glioblastoma. The term "glioma" encompasses a group of cancers that includes astrocytomas, oligodendrogliomas, oligoastrocytomas, and ependymomas. The most widely used scheme for classification and grading of glioma is that of the World Health Organization, where gliomas are classified according to their hypothesized line of differentiation, that is whether they display features of astrocytic, oligodendrial or ependymal cells. They are graded on a scale of I to IV according to their degree of malignancies. Glioblastoma (GBM) is classified as grade IV anaplastic astrocytoma.

Glioblastoma is the most common primary brain tumors in the adults. More than half of the 18,000 patients diagnosed with malignant primary brain tumors in US each year have GBM. GBM is an anaplastic, highly cellular tumor, with high proliferation indices, microvascular proliferation and focal necrosis. Signs and symptoms depend on several factors (size, rate of growth, localization of the tumor within the brain) and are mainly represented by headache, seizures, neurological deficits, changes in mental status. GBM prognosis remains dismal. Survival time is less than 2 years for the majority of patients. Karnofsky performance status (KPS) is one of the most important prognostic factors: patients with KPS>70 are alive at 18 months in approx 18% of cases, compared with 13% of patients with lower KPS scores. Primary GBM develops de novo from glial cells, typically has a clinical history of less than six months, is more common in older patients and presents small-cell histology. Secondary GBM develops over months or years from pre-existing low-grade astrocytomas, predominantly affects younger people and presents giant-cell histology.

The molecular biology of gliomas has provided new insights into the development of this disease and control of the disregulation of cell signal pathways through molecularly targeted therapies is the new therapeutic frontier.

Multiple genetic changes are involved in the development of primary and secondary GBMs and the same genetic pathways are dismantled in both primary and secondary tumors.

The main pathways involved in GBM pathogenesis are two [Rich J N, Bigner D D. Nat Rev Drug Discov 2004; 3(5): 430-46]. The first is the signalling pathway mediated by tyrosine kinase growth factor receptors: the ras-MAP kinase signal transduction cascade is activated in nearly all GBMs and Akt is activated in approximately 70% of GBMs. Indeed, amplification of many tyrosine kinase receptors has also been reported [Puputti M et al. Mol Cancer Res 2006; 4(12): 927-934].

The second pathway frequently disrupted in this pathology, as well as in many other human cancers, is the RB-CDK-CDKI (cyclin-dependent kinase inhibitor) regulatory circuit: loss of INK4A (also known as p16) is detected in 40-57% of GBMs and loss of the tumor suppressor Retinoblastoma (RB) is identified in 14-33% of GBMs. In total, mutations in INK4A/CDK2/RB are detected in more than 80% of GBMs and in 50% of anaplastic astrocytomas [Zhu Y and Parada L F. Nature Reviews Cancer 2002; 2: 616-626].

Current therapeutic options for GBM include surgery, radiotherapy and chemotherapy. Drugs most widely used are carmustine, lomustine, vincristine, procarbazine, carboplatin, etoposide and irinotecan. Neoadjuvant or adjuvant therapy with these drugs was shown to prolong disease-free survival but not overall survival.

Concurrent temozolomide (TMZ) and radiotherapy (RT) has now become the new standard of care for patients with newly diagnosed GBM, with a clinically meaningful improvement in survival compared to RT alone (median survival time of 15 months for patients treated with TMZ/RT versus 12 months for patients treated with RT alone; 2-year survival rate of 26% for the TMZ/RT group versus 10% for the RT group.

In spite of the successful introduction of TMZ, clinicians concur that further research for the development of new agents active in glioma is warranted. Indeed, there is still an unmet medical need for new potent agents for the treatment of gliomas. The present invention addresses this problem.

SUMMARY OF THE INVENTION

The invention provides a low molecular weight compound able to cross the blood-brain barrier, able to inhibit two of the main pathways involved in glioma pathogenesis through inhibition of CDKs and of tyrosine kinase growth factor receptor-mediated signalling pathways and efficacious in inhibiting glioma proliferation.

The compound of the present invention showing the desired activity is a pyrazoloquinazoline designed to target the ATP pocket of protein kinases. The compound has revealed to be a potent ATP-competitive inhibitor of CDKs. Unexpectedly, the compound has been found to display a significant inhibitory potency towards TRKA (Thropomyosin Receptor Kinase A). Furthermore, the compound has been found able to enter in the brain in high amount.

In view of its biological activity, the compound of the invention offers a new path for the development of a treatment for the patient population suffering from gliomas.

DETAILED DESCRIPTION OF THE INVENTION

In a first aspect, the present invention relates to a compound of formula (I)

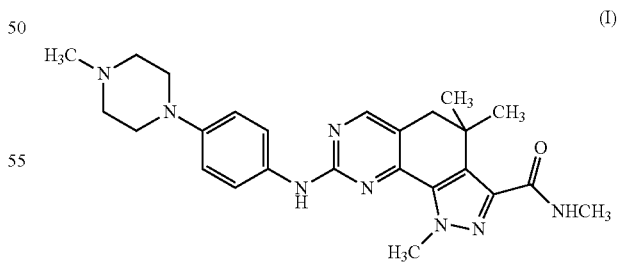

or a pharmaceutically acceptable salt thereof for use in a method for treating a malignant glioma.

As used herein the term "malignant glioma" or "glioma" includes astrocytomas (in particular glioblastomas), oligodendrogliomas, oligoastrocytomas, ependymomas as well as mixed glio-neuronal tumors (tumors displaying a neuronal as well as a glial component, e.g. gangliogliomas, disembryoplastic neuroepithelial tumors) and tumors originating from neuronal cells (e.g. gangliocytoma, central gangliocytoma).

In a preferred embodiment of the invention the compound of formula (I) as defined above is used in a method for treating a glioblastoma (GBM).

The compound of formula (I) has the chemical name 8-[4-(4-methyl-piperazin-1-yl)-phenylamino]-1,4,4-trimethyl-4,5-dihydro-1H-pyrazolo[4,3-h]quinazoline-3-carboxylic acid methylamide. It can be prepared as described in WO2004104007, is endowed with protein kinase inhibitory activity and is thus useful in therapy as antitumor agent. In particular, the preferred preparation of the compound of formula (I) is that described in example 58 of the above mentioned International Patent Application.

Pharmaceutically acceptable salts of the compound of formula (I) include the acid addition salts with inorganic or organic acids, e.g., nitric, hydrochloric, hydrobromic, sulphuric, perchloric, phosphoric, acetic, trifluoroacetic, propionic, glycolic, lactic, oxalic, malonic, malic, maleic, tartaric, citric, benzoic, cinnamic, mandelic, methanesulphonic, isethionic and salicylic acid and the like.

Within the scope of the claimed invention is the use of all the possible isomers and their admixtures and of both the metabolites and the pharmaceutically acceptable bio-precursors (otherwise referred to as pro-drugs) of the compounds of formula (I). Prodrugs are any covalently bonded compounds, which release the active parent drug, according to formula (I), in vivo.

A therapeutically effective amount of the compound according to formula (I) may be administered to a subject upon determination of the subject as having a disease or unwanted condition that would benefit by treatment with said compound. Medical or clinical personnel may make the determination as part of a diagnosis of a disease or condition in a subject. The compound may also be used in the prevention of such conditions, which may be viewed as reducing the probability of a subject having one or more of the conditions.

As used herein, a "therapeutically effective amount" of a compound refers to an amount sufficient to achieve its intended purpose. Determination of the effective amounts is well within the capability of those skilled in the art based upon the achievement of a desired effect. An effective amount will depend on factors including, but not limited to, the size of a subject and/or the degree to which the disease or unwanted condition from which a subject suffers has progressed. The effective amount will also depend on whether the compound is administered to the subject in a single dosage or periodically over time.

The compound of formula (I) of the present invention is intended for the treatment of subjects. As used herein, the term "subject" encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs and cats; laboratory animals including rodents, such as rats, mice and guinea pigs, and the like. Examples of non-mammals include, but are not limited to, birds, fish and the like.

The term "treating" as used herein includes achieving a therapeutic benefit. By therapeutic benefit is meant eradication or amelioration of the underlying disorder being treated. For example, in a cancer patient, therapeutic benefit includes eradication or amelioration of the underlying cancer. Also, a therapeutic benefit is achieved with the eradication or amelioration of one or more of the physiological symptoms associated with the underlying disorder such that an improvement is observed in the patient, notwithstanding the fact that the patient may still be afflicted with the underlying disorder.

Another object of the present invention is a therapeutic combination comprising the compound of formula (I) as defined above and (b) one or more antineoplastic agents selected from the group consisting of cytotoxic or cytostatic chemical agents and ionizing radiation, for use in a method for treating a malignant glioma.

Exemplary cytostatic or cytotoxic chemical agents includes antibiotic-type agents, alkylating agents, antimetabolite agents, antimicrotubules agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

In a particularly preferred embodiment of the invention the cytotoxic or cytostatic chemical agent is temozolomide.

Ionizing radiation, also referred to as radiotherapy, is conventionally adopted in the therapeutic field of cancer treatment and includes photons having enough energy for bonds ionization such as, for example, alpha-, beta- and gamma-rays from radioactive nuclei as well as X-rays.

The present invention also relates to a pharmaceutical composition comprising a compound of formula (I) as defined above admixed with a pharmaceutically acceptable carrier, diluent or excipient, for use in the treatment of malignant gliomas.

In a further embodiment the pharmaceutical composition according to the invention further comprises one or more antineoplastic agents selected from the group consisting of cytotoxic or cytostatic chemical agents and ionizing radiation. In a particularly preferred embodiment, the chemical agent is temozolomide.

The pharmaceutical compositions containing the compounds of the invention are usually prepared following conventional methods and are administered in a suitable pharmaceutical form.

For example, the solid oral forms may contain, together with the active compound, diluents, e.g., lactose, dextrose, saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine, methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions or suspensions.

As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose or polyvinyl alcohol.

In therapeutic use, the compound of formula (I) is administered to a subject at dosage levels of from about 10 mg/m$^2$ to about 600 mg/m$^2$ of body surface per day. A dosage level of from about 20 mg/m$^2$ to 200 mg/m$^2$ constitutes a particularly suitable range. For an adult human subject, a dosage of from about 20 mg to about 1000 mg per dose, more preferably from about 60 mg to about 400 mg per dose, from 1 to 28 consecutive days, may be used as a non-limiting example. Other examples of administration schedules are: daily on days 1 to 7 of a two-weeks cycle; daily on days 1 to 4 in each of three consecutive weeks of a four-weeks cycle; daily on days 1 to 14 of a three-weeks cycle; daily on days 1 to 7 and 15 to 21 of a four-weeks cycle.

Lower or higher doses than those disclosed herein may be used, as required. Such dosages, however, may be altered depending on a number of variables, not limited to the activity of the compound used, the condition to be treated, the mode of administration, the regimen of treatment, the requirements of the individual subject, the severity of the condition being treated and the judgment of the practitioner. The foregoing ranges are merely suggestive, as the number of variables in regard to an individual treatment regime is large and considerable excursions from these recommended values are not uncommon.

With the aim to better illustrate the present invention, without posing any limitation to it, the following examples are now given.

EXAMPLES

Example 1

Figure 1:
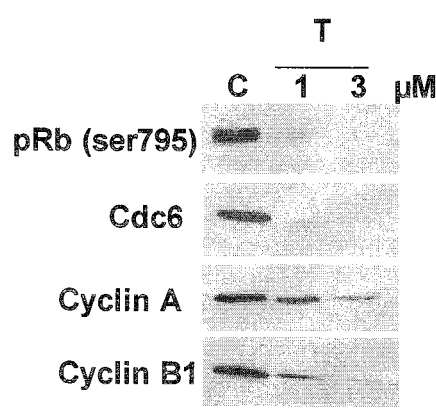
FIG. 1 illustrates protein expression in untreated cells (C) and in cells treated with two doses (1 and 3 μM) of the compound of formula (I) (T). Proteins involved in the control of cell cycle progression (cdc6; Cyclin A and Cyclin B) as well as the phosphorylation of the direct substrate of CDK2 (RB protein) were analysed.

Scintillation Proximity Assay (SPA) Format for Kinases

This assay allows measurement of the inhibition of the kinase activity of a specific enzyme obtained with test compound. Different kinases can be tested in parallel.

A biotinylated substrate is trans-phosphorylated by a specific kinase in the presence of ATP including a γ33-ATP tracer. At the end of the reaction the phosphorylated substrate is then captured using Streptavidin-coated SPA beads. A dense 5M CsCl solution is added and the mixture is incubated for four hours. This causes the SPA beads to float to the top of the CsCl solution containing the unincorporated radiolabelled ATP. The extent of phosphorylation is measured using a β-counter.

In these assays, the compound of formula (I) showed a potent inhibitory activity on the CDK2/Cyclin A complex (IC$_{50}$=45 nM), showing activity also towards closely related CDKs, i.e. CDK1, CDK4, and CDK5 ((IC$_{50}$=398, 160 and 265 nM, respectively), but also towards Thropomyosin Receptor Kinase A (TRKA) (IC50=53 nM).

Example 2

Levels of Compound of Formula (I) in the Brain

Han Wistar rats were treated for 6 consecutive days with an oral administration of compound of formula (I) at the dose of 60 mg/kg. The animals were sacrificed on day 6 at 2 and 6 hours after dosing. Brain and plasma were taken at the sacrifice time. Blood was put in heparinised plastic tubes, kept in ice-water bath, and then centrifuged (10 minutes, 1200 g at 4° C.). Brain and plasma samples were stored in a freezer at −80° C. until analysis. The levels of compound of formula (I) were analysed by LC/MS/MS.

Brain levels of the compound of formula (I) resulted to be on average 88.9 and 69.4 nmoles/gr of tissue at 2 and 6 hours post-dosing. The corresponding levels in plasma are 9.8 and 8.4 nmoles/mL, respectively. Assuming a density equal to 1, brain levels of the compound of formula (I) are 6.1-9.6 times higher than plasma levels.

Example 3

Determination of Radioactivity Distribution in Brain by Autoradioluminography Following Administration of [14C]-Labelled Compound of Formula (I) to Sprague Dawley Rats

[14C]-labelled compound of formula (I) (specific activity of 5 μCi/mg, prepared in house) was administered by single oral administration (20 mg/kg as maleate salt, approximately 3.7 MBq/kg, 100 mCi/kg as radioactive dose) to 6 male albino rats (Sprague Dawley rats from Charles River Italy; body weight at the dosing 259-273 g).

Animals were sacrificed 2, 6 and 24 hours after administration (2 animals at each selected time) and the radioactivity distribution of compound-related material was evaluated in intact brain, after excision. The autoradioluminography method was used to evaluate the quantitative radioactivity distribution in the brain.

The radioactivity distribution was also evaluated in blood and plasma collected from the animals after sacrifice. The radioactivity levels in blood and plasma were determined by Liquid Scintillation Counting (LSC).

Table 1 shows the distribution of 14C-labelled compound of formula (I) after single oral dosing (20 mg/kg) in rat.

TABLE 1

| Tissue | μg eq/g | | |
| --- | --- | --- | --- |
|  | 2 h | 6 h | 24 h |
| Brain (total radioactivity) | 4.6 | 1.4 | 0.4 |
| Cerebellum (total radioactivity) | 4.4 | 1.5 | 0.4 |
| Plasma (total radioactivity) | 1.43 | 0.89 | 0.14 |

Example 4

Effect of Compound of Formula (I) in Glioma Cells in vitro

SF-268, SF-295, SF-539 and U251 cell lines were cultured in RPMI 1640 added with 10% FCS and 2 mM glutamine and U-87MG cell line was cultured in EMEM added with 10% FCS, 2 nM glutamine and 1% NEAA. For all the experiments cells were seeded at the density of $1 \times 10^4/cm^2$, the day after treatment with the compound for the prescribed duration and then collected at the reported times.

Inhibition of Cell Proliferation.

Cells were washed and counted 72 hours after the treatment. Cell proliferation was determined by a cellular adenosine triphosphate monitoring system. Cell proliferation was compared to control cells. The concentration inhibiting cell proliferation by 50% ($IC_{50}$) was calculated.

Analysis of BrdU Incorporation.

BrdU (5-bromo-2' deoxyuridine) was added to the cell culture at the final concentration of 30 µM for the last hour of a 24 hour-treatment. Cells were washed with PBS, fixed in 70% ethanol and stored at −20° C. At the moment of the analysis cells were centrifuged, washed with 1% FCS in PBS and DNA denaturated with HCl 2N for 20 minutes. After a wash in $Na_2B_4O_7$ 0.1M pH 8.5, cells were incubated with a solution of 0.5% Tween20 in PBS+1% FCS for 15 minutes and then centrifuged. The pellets were resuspended in 150 µl of a 1:10 diluted unconjugated anti-BrdU monoclonal antibody (Becton Dickinson) and incubated for 1 hour at room temperature. After a wash in PBS, the incubation with 0.5% Tween20 was repeated; then the secondary antibody was added (1:50 diluted FITC-conjugated goat anti mouse immunoglobulin (Jackson Lab.)). After one hour at room temperature the cells were rinsed again, counterstained with propidium iodide (2 µg/ml+12.5 µg/ml DNAse-free RNAse) overnight, then analyzed by FACS.

Acridine Orange Staining to Evaluate Autophagy.

During the last 15 minutes of incubation, acridine orange (1 µg/ml) was added to the cells that were then collected, washed with PBS and analyzed by FACS for their fluorescence emission. Acridine orange moves freely to cross biological membranes but, when in the cytoplasm and nucleolus, fluoresces bright green and dim red; in the acidic vacuoles generated by autophagy appears bright red.

The results of all these assays are reported in Table 1. The compound of formula (I) is active on all the tested glioma cells (first column): it is able to inhibit proliferation with an $IC_{50}$ in the range 1.4-5.4 µM (second column), it has an effect on DNA synthesis measured as inhibition of BrdU incorporation ranging from 39 to 92% (third column) and it is able to induce autophagy in 36-70% of the cells (fourth column). This kind of tumors has been reported to preferentially undergo autophagy in response to chemotherapy and γ-radiations instead of apoptosis.

TABLE 2

| Glioma | $IC_{50}$ (µM) | % BrdU inhib | Autophagy % |
|---|---|---|---|
| U251 | 2.8 +/− 0.8 | 74 | 58 (3 µM) |
| SF539 | 1.4 +/− 0.5 | 39 | 35 (6 µM) |
| SF268 | 2.5 +/− 0.6 | 78 | 70 (3 µM) |
| SF295 | 5.4 +/− 0.6 | 74 | 68 (3 µM) |
| U87MG | 1.6 +/− 0.8 | 92 | 50 (3 µM) |

Example 5

Evaluation of Compound of Formula (I) Mode of Action by Western Blot Analysis

Treated cells were lysed by adding SDS sample buffer (0.125M Tris-HCl pH6.8, 5% SDS). Samples were heated to 95° C. for 5 minutes and then sonicated using an Ultrasonic 2000 ARTEK. Lysed cells were centrifuged at 13,000 RPM for 10 minutes. Protein quantification was determined using BCA buffer (Pierce) and a BSA standard curve. 20 µg protein extract per well were loaded and separated by SDS-PAGE gel 7.5-10% (PAGE-PLUS 40% concentrate AMRESCO). The gel was blotted onto nitrocellulose filters (Hybond Amersham) in a buffer containing 25 mM Tris HCl pH 8.3, 192 mM Glycine and 20% methanol. The filters were saturated in 5% low-fat milk in TBS containing 0.1% Tween 20 (TBS-T) for 2 hours at room temperature and than incubated overnight at 4° C. with the primary monoclonal followed by washes in TBS-T and incubation using a secondary anti mouse antibody. The bands were visualized using the "Super Signal West Pico" Pierce.

The results obtained in all the tested cell lines showed that the compound of formula (I) is able to interfere with both the main pathways involved in glioma pathogenesis. In fact, a decrease in the cell cycle related markers is observed in all glioma cell lines independently from the status of Rb pathway. FIG. 1, as example, shows the results obtained with two doses of compound of formula (I) in U251 cells treated for 24 hours. A strong inhibition of Rb phosphorylation as well as of cdc6, cyclin A and B1 expression is evident.

Figure 2:
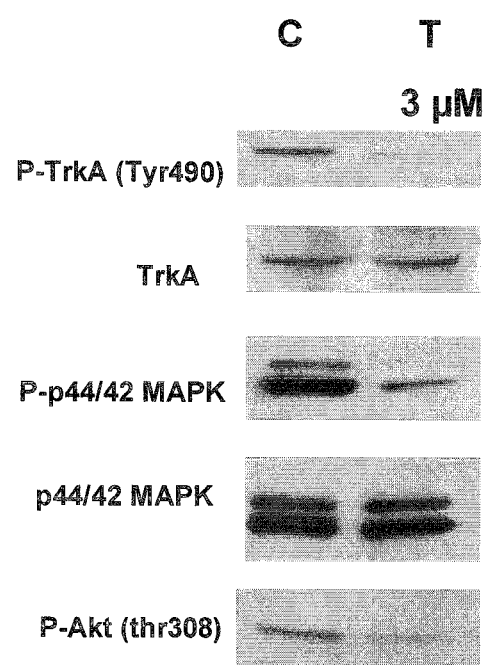
FIG. 2 illustrates protein expression in untreated cells (C) and in cells treated with 3 μM of the compound of formula (I) (T). Amount of phosphorylated TRKA, total TRKA protein, phosphorylated p44/42MAPK and AKT and total p44/42MAPK were shown.

The ability of compound of formula (I) to inhibit also the pathway mediated by tyrosine kinase growth factor receptors was also evaluated. Inhibition in phosphorylation of TRKA receptor and of downstream proteins, both in the MAPK and in AKT pathway, is shown in FIG. 2 in SF-539 cells treated for 6 hours.

Example 6

Effect of Compound of Formula (I) in Glioma Cells in vivo

Antitumor Efficacy on a Xenograft Model of Human Glioma

Balb, Nu/Nu male mice, from Harlan (Italy), were maintained in cages with paper filter cover, food and bedding sterilized and water acidified. $2.5 \times 10^6$ U251 human glioma cells (from the American Type Culture Collection) were injected subcutaneously in athymic mice. Compound of formula (I) was administered by oral route in a volume of 10 ml/kg at the dose of 40 mg/kg twice a day (BID) for 10 consecutive days. Tumor growth and body weight were measured every 3 days. Tumor growth was assessed by caliper. The two diameters were recorded and the tumor weight was calculated according the following formula: length (mm)× $width^2/2$. Toxicity was evaluated on the basis of body weight reduction.

Results reported in Table 2 shows that the compound of formula (I) produced a clear antitumor effect in the human glioma xenograft model U251.

TABLE 3

| Treatment | Max tumor growth inhibition (%) | Toxicity |
|---|---|---|
| Compound of formula (I) 40 mg/kg | 80 | 0/8 |

Efficacy on Intracranially Implanted Glioma Tumor Model

Animals that underwent surgical procedures were anesthetized following one of the above mentioned protocols, i.e. Ketamin, 80-100 mg/kg i.p.+Xilazin: 10 mg/kg i.p.; Isofluorane: 1.5-2%. Athymic male nude mice, aged 6-8 weeks were anesthetized, placed under the stereotaxic apparatus and gently fixed with ear bars and into the head holder. Skin of the head was cut longitudinally (parallel to ears) and skull of the mouse discovered. With the X and Y axis controller of the apparatus, bregma (interception between median sagittal and anterior coronal sutures to perform injection into the cerebral nuclei) and lambda (interception between median sagittal suture and posterior coronal suture to perform injection into the cerebellum) were identified as point 0. The following coordinates were set in the apparatus and the point of injection identified. With a microdrill a small hole was done in the desired point. Cells were aspirated with the Hamilton syringe (usually 2-5 ml) just prior injection (a short mix of cells before aspiration was performed to avoid precipitation of cells). By pointing to the hole, Z axis was fixed to 0 and syringe gently inserted into the brain until reaching the right coordinate (−3.0 mm depth). U251 cells were injected at the speed of 1 µl per minute. The syringe was left for additional 5 minutes in the hole before removing it to avoid cell aspiration. Hole was closed using bone wax and the wound with sterile autoclips. After the end of the surgery mice were monitored for recovery until complete wakening.

Figure 3:
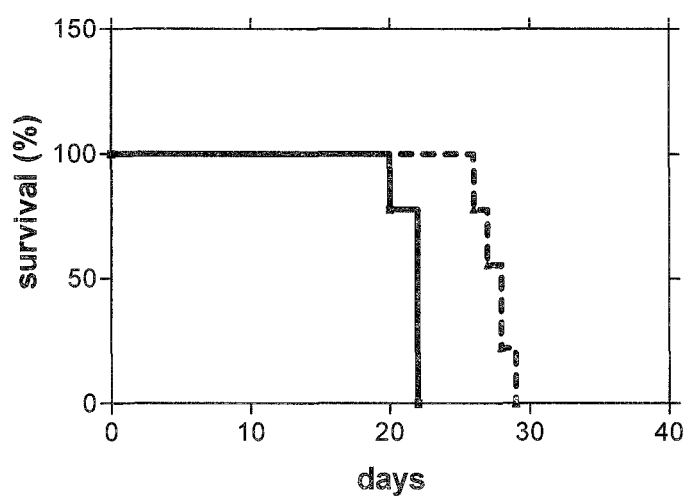
FIG. 3 illustrates the survival of mice bearing the glioma cell line intracranially implanted: untreated mice (black line), mice treated with compound of formula (I) (dashed line).

The result reported in FIG. 3 shows that mice bearing a human glioma model intracranially implanted treated with compound of formula (I) at the dose of 40 mg/kg bid OS present a 30% increase in the survival time in comparison to vehicle-treated control mice.

The invention claimed is:

1. A method for treating a malignant glioma, the method comprising administration of a compound of formula (I)

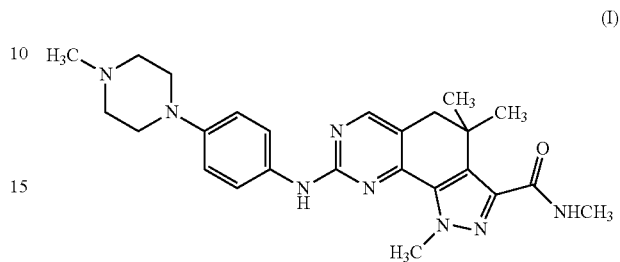

(I)

or a pharmaceutically acceptable salt thereof in combination with one or more antineoplastic agents, wherein the agent is temozolomide.

2. The method according to claim 1 wherein the malignant glioma is a glioblastoma.

* * * * *